(12) United States Patent
Fierro

(10) Patent No.: US 6,911,002 B2
(45) Date of Patent: Jun. 28, 2005

US006911002B2

(54) SLING WITH PAD FOR TREATMENT OF URINARY INCONTINENCE

(75) Inventor: Eduardo Fierro, Cordoba (AR)

(73) Assignee: Promedon S.A., Cordoba (AR)

( * ) Notice: Subject to any disclaimer, the term of this patent is extended or adjusted under 35 U.S.C. 154(b) by 120 days.

(21) Appl. No.: 10/168,554

(22) PCT Filed: Dec. 20, 2000

(86) PCT No.: PCT/EP00/13016

§ 371 (c)(1),
(2), (4) Date: Jun. 21, 2002

(87) PCT Pub. No.: WO01/45589

PCT Pub. Date: Jun. 28, 2001

(65) Prior Publication Data

US 2002/0183588 A1 Dec. 5, 2002

(51) Int. Cl.⁷ .................................................. A61F 2/02
(52) U.S. Cl. ......................................................... 600/30
(58) Field of Search .............................. 600/29–31, 573, 600/38, 39, 41; 128/885, 842, 894, 825; 606/151

(56) References Cited

U.S. PATENT DOCUMENTS

| | | | | |
|---|---|---|---|---|
| 4,632,114 A | * | 12/1986 | Todd et al. | .................... 600/31 |
| 5,766,183 A | * | 6/1998 | Sauer | .......................... 606/139 |
| 6,042,534 A | * | 3/2000 | Gellman et al. | .............. 600/30 |
| 6,695,856 B2 | * | 2/2004 | Kieturakis et al. | .......... 606/151 |

FOREIGN PATENT DOCUMENTS

| | | | | |
|---|---|---|---|---|
| WO | WO 00/74633 A2 | * | 12/2000 | .................. 600/30 |

* cited by examiner

*Primary Examiner*—Samuel G. Gilbert
(74) *Attorney, Agent, or Firm*—Bachman & LaPointe, PC

(57) ABSTRACT

The present invention relates to a sling (1) for treatment of urinary incontinence, consisting of a band (2) which comprises a middle part (3) and two end parts (4), the said sling including, on its middle part (3), at least one pad (6) with which it is possible to reduce, or even eliminate, the friction between the sling and the organs in contact with the said sling.

28 Claims, 7 Drawing Sheets

SLING WITH PAD FOR TREATMENT OF URINARY INCONTINENCE

The present invention relates to a sling for treating urinary incontinence in women and men. It concerns more particularly a sling having one or more pads, and a kit which contains such a sling in a sterile manner.

Urinary incontinence affects many people, men after prostatectomy, and mainly women. Four types of urinary incontinence have been defined by the International Continence Society: stress, urge, overflow and reflex incontinence.

The first type and the more frequent, called stress incontinence, takes place during straining, following laughing or coughing, or during physical exercise. It results from weakness of the urethral sphincter which is no longer able to seal off the bladder, due to a loosening of the muscles of the perineum and/or Intrinsic Sphincter Deficiency (ISD). This form of incontinence can occur after childbirth or at the menopause, but it can also affect young sportswomen overdeveloping their abdominal muscles to the detriment of the perineum or in neurogenyc bladder such as myelomeningocele.

The second more frequent form of incontinence, referred to as overactive bladder, results from involuntary contractions of the (hyperactive) bladder and is manifested in an excessively frequent and irrepressible urge to urinate.

Some women suffer from mixed incontinence, which is a combination of the forms mentioned above.

Overactive bladder can be cured by taking medication aimed at relaxing the bladder.

For treating stress incontinence or preventing this incontinence, it is often necessary to resort to surgery.

The techniques known from the prior art consist in restoring the natural mechanisms of continence: in maintaining the urethra in the abdominal cavity and/or in increasing urethral resistency. To do this, a sling has already been used which is placed under the bladder neck or under the urethra, thereby making it possible to improve the suspension and some compression of the bladder neck and/or of the urethra.

Thus, application WO 98/35632 describes a stabilization sling for use in minimally invasive pelvic surgery and designed for urethral suspension, and U.S. Pat. No. 5,934,283 concerns a pubovaginal sling device.

However, the slings used hitherto may, in some cases, cause friction in the area of the vagina, urethra or bladder. The reason for this is that during movements, the said slings may injure the different organs with which they are in contact. This friction in the area of the vagina, urethra or bladder may then cause erotions, inflammations or infections, or even cause rejection of the sling and make it necessary to remove the said sling, and, consequently, to perform a new operation.

It has thus been found that it is necessary, in one woman in every seven in the highest series of complications, to proceed with a new operation for removing the said sling. The percentage of sling extraction due to rejection and erosion ranks from 3 to 22%. This is sustained by the following references:

D. Myers and C. La Sala, "Conservative surgical management of mersilen mesh suburethral sling erosion", AM.J.OBSTET.GYNEC., December 1998-Vol 179, n° 6, part 1.

Summit, "Suburethral sling procedure for genuine stress incontinence and low urethral clossure pressure: a continued experience", UROGYNECOL.J-1992, 3, 18–21.

Weinberger, Mostergard D., "Long term clinic and urodynamic outcomer of PTFE suburethral sling for treatment of genuine stress incontinence", OBSTET.GYNECOL-1995, 86, 92–6.

Bent, Ostergard, Zwick, Zafutto, "Tissue reaction to expanded PTFE suburethral sling for urinary incontinence: clinical and histologic study", AM.J.OBSTET.GYNEC., 1993-Vol 169,1198–204.

Young et al, "The mersilene mesh suburethral sling: a clinical and urodynamic evaluation", AM.J.OBSTET.GYNEC., December 1995-Vol 173, n° 6.

M. Corujo, G. Badlani, "The use of synthetic material in the treatment of women with SUI lends strength and durability", CONTEMPORARY UROLOGY, March 1999, vol.11, n° 3-PP, 76–81

Yue Kim Chin, Stuart Stanton, "A follow up of silastic sling for genuine stress incontinence", BRITISH JOURNAL OF OBSTETRICS AND GYNAECOLOGY, February 1995, vol 102, 143–147.

The aim of the present invention is to propose novel slings which avoid these disadvantages, that is to say slings which are better tolerated by the body and thus have less risk of erosion than those in the prior art, with low risk of rejection and obvious benefits for patients, such as for example obviating the need to remove the said sling and thus not requiring a new operation.

The subject of the present invention is therefore a sling for treatment of urinary incontinence, consisting of a band which comprises a middle part and two end parts, the said sling including, on its middle part, at least one pad with which it is possible to reduce, or even eliminate, the friction between the sling and the organs in contact with the said sling.

According to one embodiment of the invention, the band is made of silicone. In a preferred embodiment, this silicone contains a reinforcement which, according to a particular embodiment of the invention, consists of a polyester mesh.

For the surgeon's convenience, the band may be developed long enough to remove the surplus without damaging the sling structure.

The pad can be full or in the form of a capsule.

In a preffered embodiment of the invention, the pad is entirely made of silicone foam which can be covered by a cuticle of biocompatible material.

When the pad is under the form of a capsule, the capsule is made of a biocompatible material such as silicone, polyurethane, etc. This capsule can contain air, water, physiological solution, PVP (Polyvinylpyrrolidone), silicone oil or gel, or any other biocompatible liquid.

In a preferred embodiment of the invention, the thickness of the pad is at least twice as great as the thickness of the band.

In one embodiment of the invention, the pad is fixed on the middle part using a biocompatible adhesive such as a silicone adhesive, depending on the material to be adhered. The pad will also be able to be fixed on the middle part by heat-sealing or by any suitable fixing means.

According to a further embodiment of the invention, the said sling is additionally provided with two extensions of the band, localized under the pad and on each side of the band. These extensions can be used to fix with the suture the sling to the urethra/bladder neck; they can also be used as visual markers.

According to another embodiment of the invention, the said sling is additionally provided with at least one visual marker. For example, it may be provided with one or more visual markers for X-ray observations during surgery or for post-surgery control in order to establish if the sling has moved.

In another embodiment of the invention, the sling is entirely or partly impregnated with or covered by a biocompatible substance, for example an antibiotic.

The end parts of the sling can be provided with securing means.

According to an embodiment of the invention, the securing means consist of perforations; the circumference of these perforations can be reinforced.

According to a preferred embodiment of the invention, the sling fixation is performed by suturing or joining both ends of the sling. The sutures used may be non-absorbable monofilaments, such as propylene types.

The end parts of the sling can also be provided with means permitting or faciliting the suturing or joining of both ends of the sling.

Another subject of the invention is a kit containing, in a sterile manner, at least one sling according to the invention.

The sling will be able to be packaged and/or immersed in a solution of antibiotic, such as neomycin.

The surgical methods for fitting the slings according to the invention are those known to the person skilled in the art. To this end, reference is made to U.S. Pat. No. 5,611,515 (Benderev et al.), to U.S. Pat. No. 5,934,283 and to application WO 98/35632, describing the different methods that can be used. Those using minimally invasive pelvic surgery are particularly preferred.

The sling can be fixed, in a prefered method, in front of the abdominal aponeurosis, suturing both ends of the sling, or be fixed to the right and left couperligament. It is also possible to do an independent fixation to the aponeurosis pubic insertion of the abdominal muscles, or by using anchors systems.

Besides the fixing systems previoulsy mentioned, the sling can be also fixed to the abdominal fascia without suture (Autofixing System). In this case, instead of having two bands by each side of the pad, the sling has two columns cone-shaped. The columns may also have different shapes such, for example, fish-hook. The columns can also be multispheric, being the spheres of the same or different sizes, interchanging those sizes all along the columns. The columns are made of biocompatible synthetic materials, preferably silicone. The shape particularly conical of the columns makes them fix by themselves to the muscles, thus immobilizing the sling. This autofixing of the sling is improved after the implantation surgery because of the resulting fibrosis that eventually wrapes the whole sling.

Figure 1:
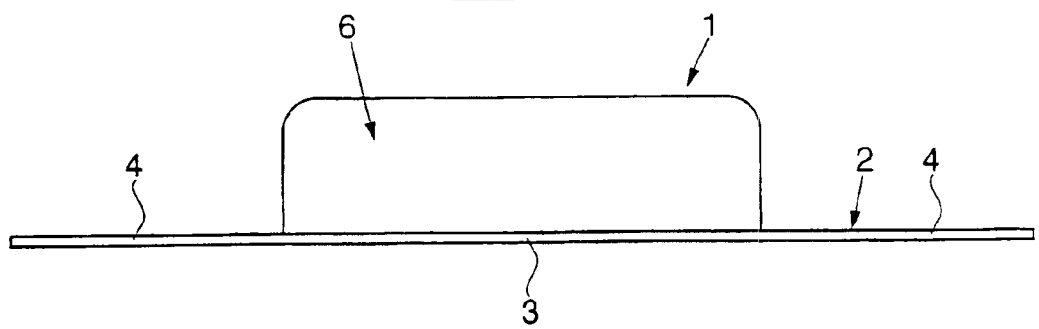
FIG. 1 is an elevation view of a sling according to the invention.

FIG. 1 is an elevation view of a sling (1) according to the invention. This sling consists of a band (2) which comprises a middle part (3) and two end parts (4). This sling includes, on the middle part (3), a pad (6) with which it is possible to reduce, or even eliminate, the friction between the sling and the organs in contact with the said sling.

The organs in contact with the sling are in particular the vagina, the urethra, the bladder or the bladder neck. The sling lies on the urethra, producing a coaptation of 180°.

The material from which the band (2) is made can be any biocompatible biological or synthetic material. It can be filamentous or non-filamentous, elastic or non-elastic, porous or microporous, perforated or impermeable. This material may be chosen depending on the properties sought, in particular to facilitate the surgical intervention and prevent any risk of rejection.

Thus, this material may be chosen from pericardium, a polyester, a polypropylene, a polyurethane, a nylon, a collagen, a silicone, a polytetrafluoroethylene, such as Teflon, a polyethylene terephthalate or a latex. In the case of fibrous materials, the latter may be woven or non-woven. Thus, it will be possible to use polyester meshes. It will also be possible to use a mixture of these different materials, for example a mixture of a silicone and Dacron, or a silicone reinforced by a polyester mesh. All the materials cited in application WO 98/35632 may in particular be used.

It will be possible for the pad to be made of the same material as that used for the band or of another material. When the same material is used, the middle part, the ends and the pad may be made in one piece, for example by moulding.

The material used for the pad is adapted to make it possible to reduce or even eliminate the friction between the sling and the organs in contact with the said sling. Thus, all biocompatible materials making it possible to limit the friction and to better cushion the said organs may be used.

The pad may be made of PVA (polyvinyl alcohol), polyurethane or any bio-compatible polymer. The pad is preferably made of silicone foam.

When the pad is under the form of a capsule, it can contain air, water, physiological solution, PVP, silicone gel or oil, antibiotic solution or any other bio-compatible fluid. It may also contain substances opaque to X-rays, such as Barium sulfate, permitting observations during surgery, or for post-surgery control, mainly in order to establish if the sling has moved.

The pad is preferably entirely made of silicone foam. The silicone foam can or not be covered by an external cuticle of biocompatible material, such as a film of silicone. The cuticle can have open micro-pores, allowing the diffusion of the body fluids to the foam or in a preffered embodiment, can be closed, i.e. without micro-pores and thus preventing the body fluids from diffusing to the interior of the pad.

In another embodiment, the said sling includes at least two pads, but preferably only one.

The thickness of the pad is at least twice as great as the thickness of the band, and still more preferably, twenty times greater than the thickness of the band. This thickness is chosen so as to obtain optimum cushioning and consequently to prevent any friction between the sling and the organs being supported.

The ends or the corners of the sling and/or the pad may, preferably, be rounded so as to avoid any injury during the operation. In a particularly preferred embodiment, the edges of the pad are rounded, thereby making it possible to reduce the risks of friction still further.

Figure 2:
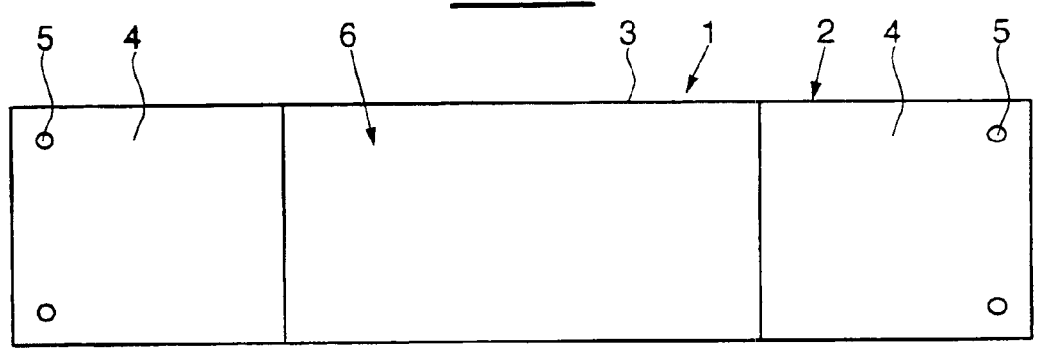
FIG. 2 is a plan view of a sling according to the invention.

FIG. 2 is a plan view of a sling according to the invention.

It will be noted that the shape of the sling represented here is rectangular. However, any elongate shape able to secure this sling in such a way that it holds the urethra and/or the neck of the bladder can be used. Thus, shapes such as rhomboids, hexagons or rectangles may be envisaged.

The optimum dimensions of this sling depend on anatomical considerations, age, sex, etc, and on the surgical method employed for introducing it and securing it. Thus, the sling may have a length of 8–60 cm, preferably 26–38 cm and a width of 1–3,5 cm, preferably 1,2–2,4 cm. Likewise, the thickness of the pad may vary between 0,15 cm and 1,8 cm and the length of the pad may vary from 4 to 10 cm.

In FIG. 2, the end parts are provided with securing means (5) consisting of perforations.

The securing means which can be used in accordance with the present invention are those which allow the said sling to be secured in such a way that it can retain and stabilize the urethra and/or the neck of the bladder.

Thus, these securing means may vary depending on the securing means used, for example pins or screws.

These securing means can also be strengthened; thus, when perforations are used, it will be possible to reinforce their circumference.

Of course, the thickness of the sling in the area of the end parts may be slightly greater than the thickness of the middle part, in such a way as to optimize the securing of the said sling and to avoid tearing the latter in the area of the end parts.

In FIG. 2, two securing means are represented at each end part. Of course, the person skilled in the art will be able to use one or more securing means at each end part, and will do this in order to facilitate the said securing and to optimize it.

The different embodiments of the securing means and of the means for reinforcing these described in application WO 98/35632 may also be envisaged in the present invention.

Figure 3:
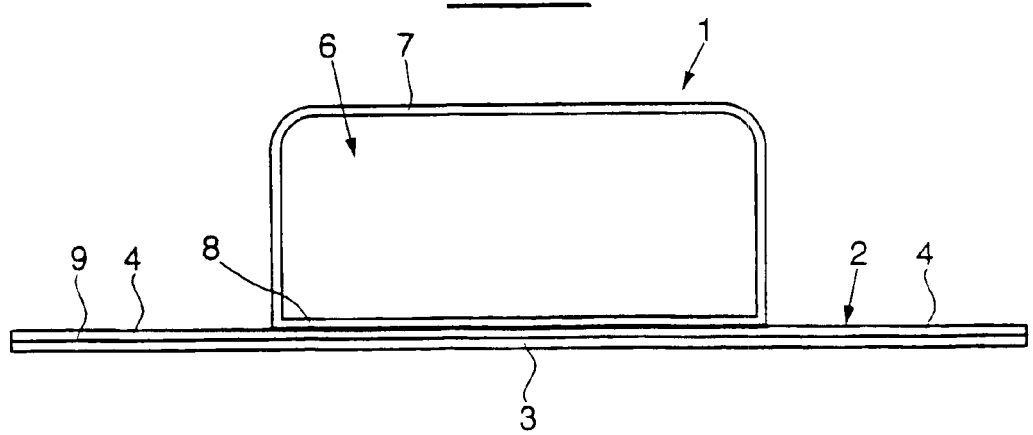
FIG. 3 is a diagrammatic longitudinal section through a sling according to a preferred embodiment of the invention.

FIG. 3 represents a longitudinal section through a sling (1) according to a preferred embodiment of the invention.

The band (2) of the sling is made of silicone. The silicone contains a reinforcement (9) at its centre, this reinforcement (9) consisting of a polyester mesh.

The pad (6) for its part is made of silicone foam covered by a cuticle (7) of biocompatible material. This cuticle of biocompatible material may, for example, be a silicone membrane. The cuticle can have open micro-pores, allowing the diffusion of the body fluids to the foam or in a preffered embodiment, can be closed, i.e. without micro-pores and thus preventing the body fluids from diffusing to the interior of the pad.

The edges of the pad are rounded.

In a preferred embodiment of the invention, the pad is fixed on the middle part using a biocompatible adhesive (8), such as silicone, cyanoacrylate or methylmethacrylate. Of course, any fixing means can be used, one example which may be mentioned being heat-sealing.

Figure 4:
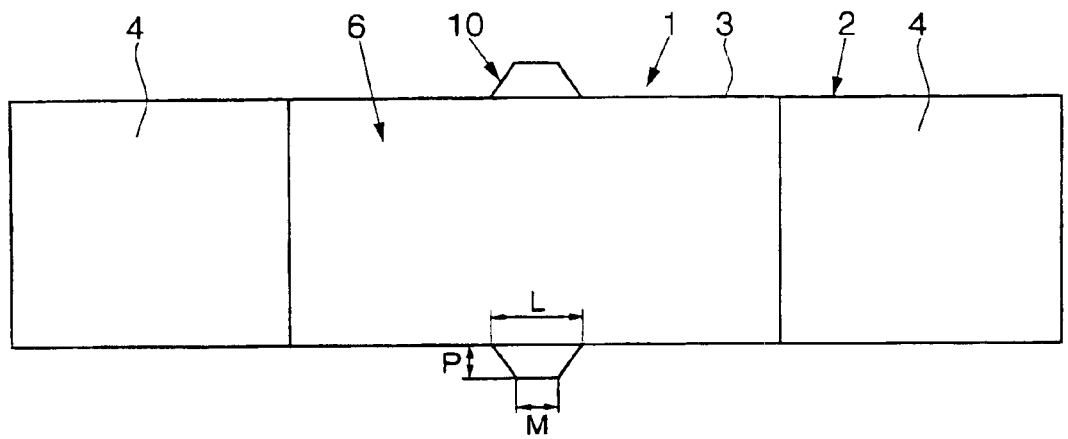
FIG. 4 is a plan view of a sling according to a preffered embodiment of the invention.

FIG. 4 is a plan view of a sling according to a preferred embodiment of the invention and shows two extensions (10) of the band (2). These extensions can be used to fix with the suture the sling to the urethra/bladder neck. They can also be used as visual marker for showing the center of the sling, highly useful during the surgery.

These extensions (10) can be trapezoidal, as shown in the drawing, or rectangular, half-circled, triangular, etc.

In a preferred embodiment, the extensions (10) are trapezoidal and M may vary from 3 to 12 mm, and preferably from 4 to 8, L may vary from 6 to 24 mm, and preferably from 8 to 16, P may vary from 2 to 15 mm, and preferably from 3 to 6.

The sling may be additionally provided with at least one visual marker, such as a radiopaque marker, making it possible in particular to position the said sling during and after the operation.

It will also be possible for the sling to be entirely or partly impregnated with or covered by a biocompatible substance, for example an antibiotic or an immunosuppressant. The biocompatible substances cited in application WO 98/35632 may be used. The material or materials of the sling will thus be able to be coated with collagen which will be gradually absorbed over the course of time after the sling has been placed in the body, thereby limiting the risk of infection during the operation.

In FIG. 4, it can be noted that no securing means consisting of perforations are present on the sling.

Figure 5:
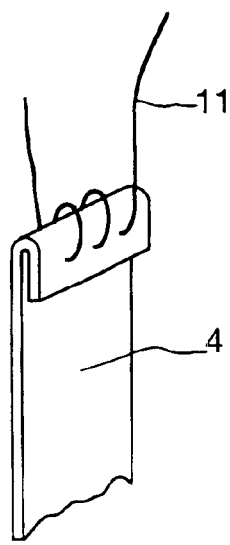
FIG. 5 is a view of one folded extreme of a sling according to the invention.

FIG. 5 is a view of one folded extreme of a sling according to the invention. The first step of the fixation of the sling can consist of suturing several times the extreme of the sling (4) previously folded. A non-absorbable monofilament (11) may be used.

Figure 6:
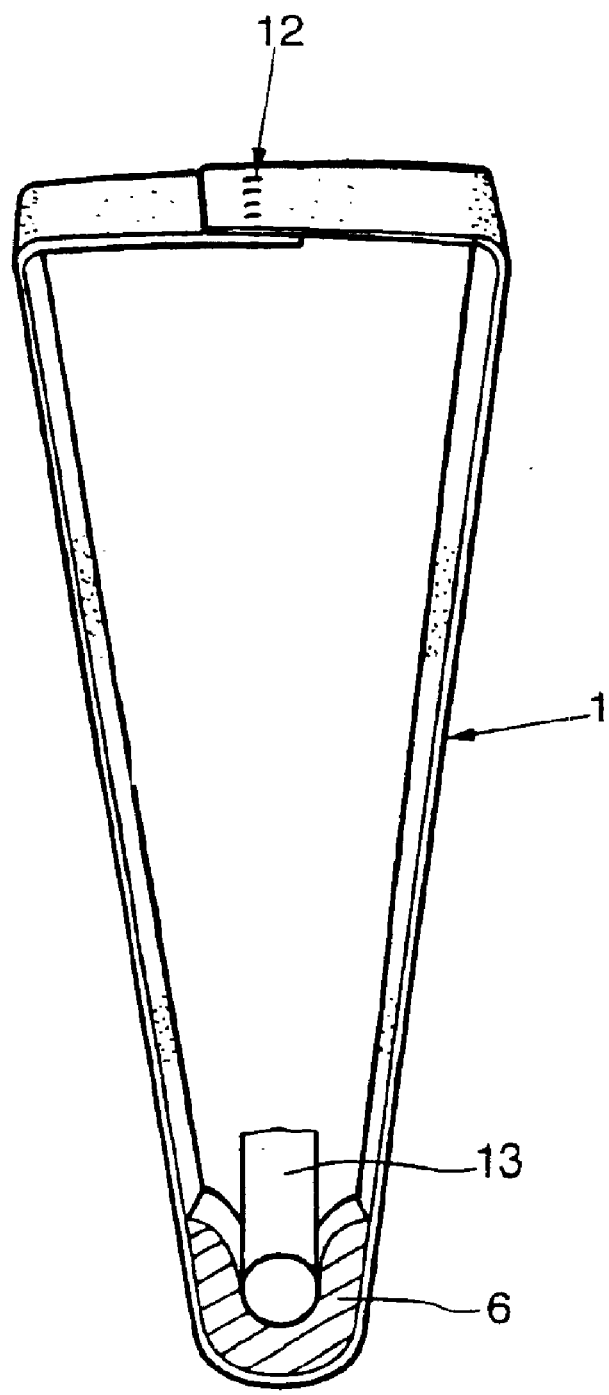
FIG. 6 is a perspective view of the sling as it would appear in place within the subject's body following surgical implantation.

FIG. 6 is a perspective view of the sling as it would appear in place within the subject's body following surgical implantation. The second step of the fixation of the sling (1) can consist of joining both extremes of the sling with a suture (12). The suture of the sling is made by joining both strips to one side, just below the line of the suprapubic incision. The suture is not realized in the middle of the sling, but in one of its sides. A method of fixation is described in U.S. Pat. No. 5,934,283. The neck of the bladder or the urethra (13) lays on the pad (6) and thus permits to reduce, or even eliminate, the friction between the sling and the neck of the bladder or the urethra (13).

Figure 7:
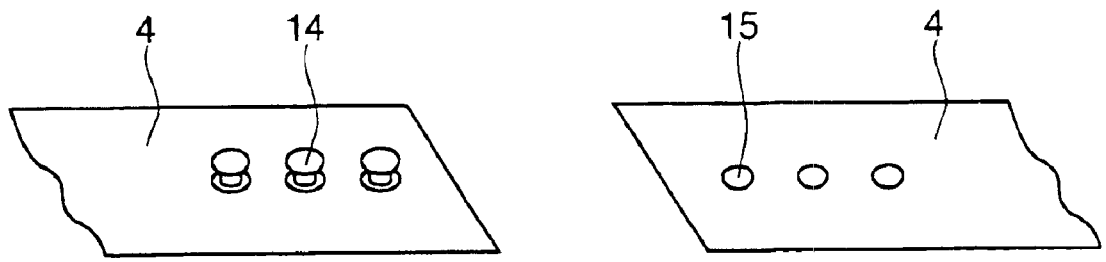
FIGS. 7, 8 and 9 show different systems permitting to join both ends of the sling.
Figure 8:
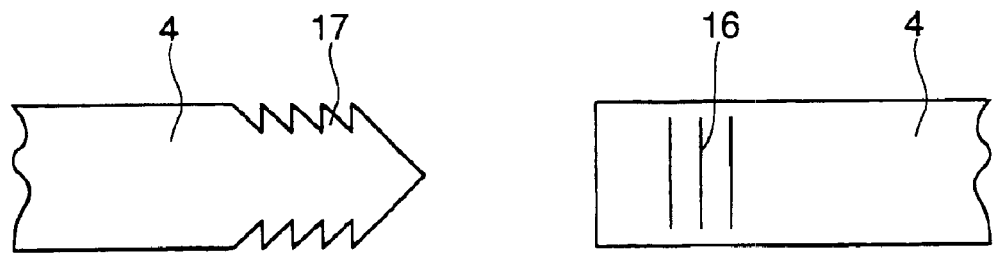
Figure 9:
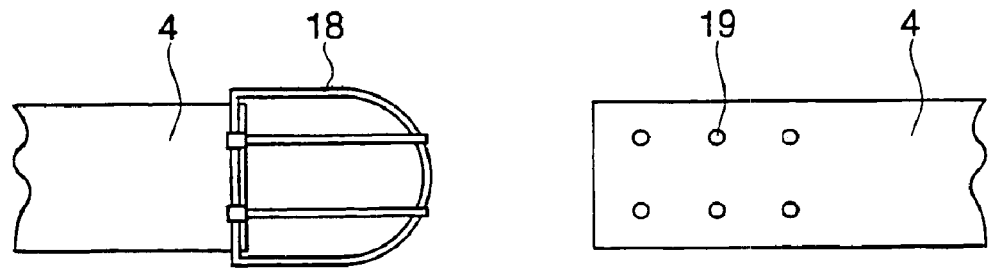

FIGS. 7, 8 and 9 show different systems permitting to join both ends of the sling, such as:

holes (15) in one extreme and buttons (14) in the other;
one of the extremes with irregular teeth (17), and holes (16) in the other;
one of the extremes with belt-like buckle (18), the other extreme being or not provided with holes (19).

Figure 10:
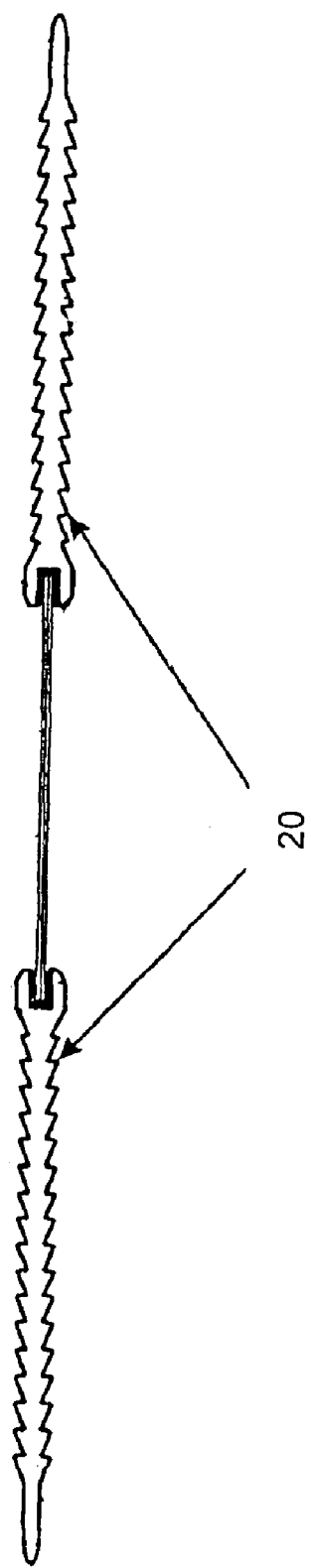
FIG. 10 is a view of a sling with autofixing system constituted by two cone-shapes columns.
Figure 11:
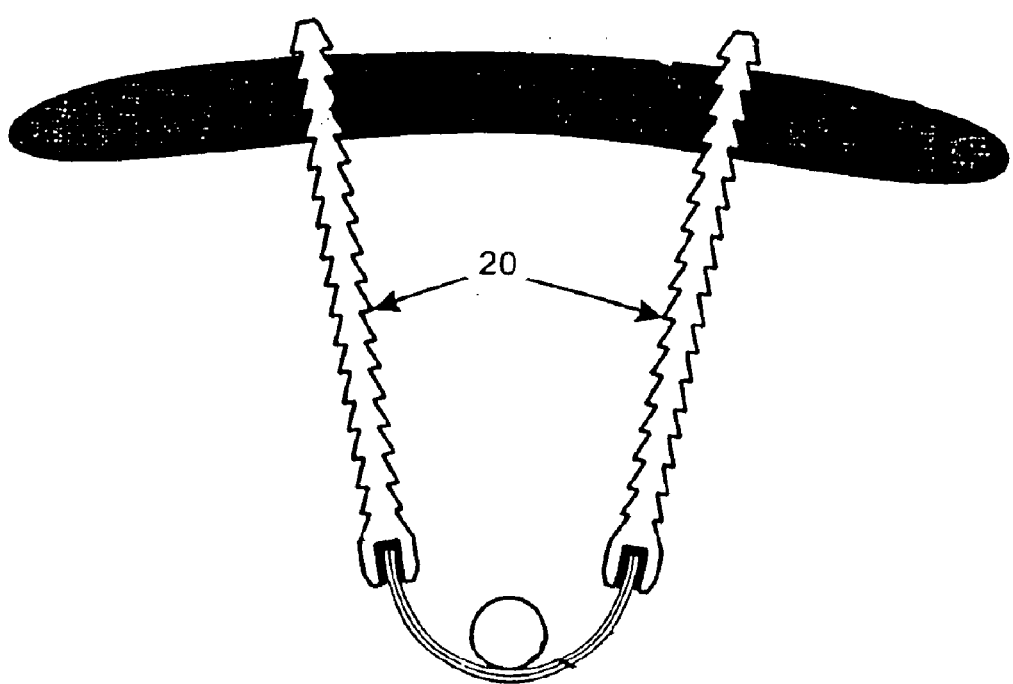
FIG. 11 is an overview of a sling with its columns for autofixing.

FIGS. 10 and 11 show a sling with its autofixing cone-shaped columns (20). These columns may have a length of 5–25 cm, preferably 20 cm. The major diameter of each cone in its base may be 2–10 mm, preferably 5 mm, and the minor diameter at the top of each cone may vary from 0.5 to 5 mm, preferably being 3 mm. The height of each cone can be 2–10 mm, preferably 4 mm.

Figure 12:
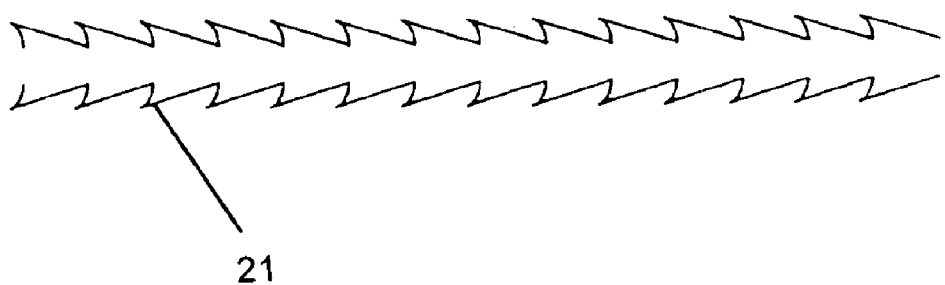
FIG. 12 is a view of a "fish-hook"-shaped column.
Figure 13:
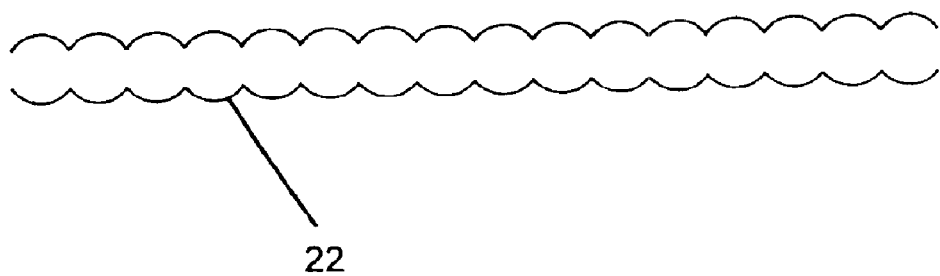
FIG. 13 is a view of different types of multispherical columns.
Figure 13:
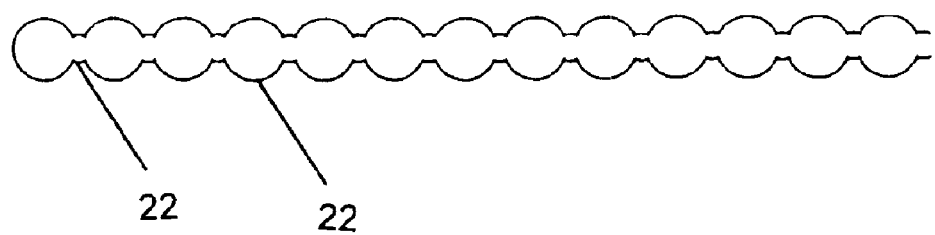

FIGS. 12 and 13 represent other types of columns to be used instead of the column 20. They may have fish-hook shapes (21) or multispheric shapes (22). Other systems permitting to join both ends can also be used by the skilled-man.

What is claimed is:

1. Sling (1) for treatment of urinary incontinence, consisting of a band (2) which comprises a middle part (3) and two end parts (4) characterized in that the sling includes, on its middle part (3), at least one pad (6) with which it is possible to reduce, or eliminate, friction between the sling and organs in contact with the sling, characterized in that the pad (6) is made entirely of silicone foam covered by a cuticle (7) of biocompatible material.

2. Sling according to claim 1, characterized in that the pad (6) is full or in the form of a capsule.

3. Sling according to claim 1, characterized in that the thickness of the pad (6) is at least twice as great as the thickness of the band (2).

4. Sling according to claim 1, characterized in that the pad (6) is fixed on the middle part (3) using a biocompatible adhesive (8).

5. Sling according to claim 1, characterized in that the band (2) is made of silicone.

6. Sling according to claim 1, characterized in that the sling is additionally provided with at least one visual marker.

7. Sling according to claim 1, characterized in that the sling is entirely or partly impregnated with or covered by an antibiotic.

8. Sling according to claim 1, characterized in that the ends of said sling are equipped with securing members (5).

9. Sling according to claim 8, characterized in that the securing members consist of perforations.

10. Sling according to claim 1, characterized in that said sling is provided with means permitting the suturing or joining of both ends of the sling.

11. Sling according to claim 10, characterized in that said sling is provided with systems permitting to join both ends, chosen among: holes in one extreme and bottoms in the other; one of the extremes with irregular teeth, and holes in the other; one of the extremes with belt-like buckle, the other extreme being or not provided with holes.

12. Sling according to claim 1, characterized in that it comprises an autofixing system.

13. Sling according to claim 12, characterized in that the autofixing system comprises two columns which are cone-shaped.

14. Sling according to claim 12, characterized in that the autofixing system comprises two columns having a fish-hook shape.

15. Sling according to claim 12, characterized in that the autofixing system comprises two columns having a multi-spheric shape.

16. Sling according to claim 12, characterized in that the autofixing system is made of silicone.

17. Sling (1) for treatment of urinary incontinence, consisting of a band (2) which comprises a middle part (3) and two end parts (4) characterized in that the sling includes, on its middle part (3), at least one pad (6) with which it is possible to reduce, or eliminate, friction between the sling and organs in contact with the sling, characterized in that the band (2) is made of silicone and contains a reinforcement (9), preferably consisting of a polyester mesh.

18. Sling according to claim 17, characterized in that the pad (6) is made of silicone foam, PVA, polyurethane or a biocompatible polymer.

19. Sling according to claim 18, characterized in that the pad (6) contains air, water, physiological solution, PVP, silicone oil or gel, antibiotic solution, substances opaque to X rays or any other biocompatible liquid.

20. Sling (1) for treatment of urinary incontinence, consisting of a band (2) which comprises a middle part (3) and two end parts (4) characterized in that the sling includes, on its middle part (3), at least one pad (6) with which it is possible to reduce, or eliminate, friction between the sling and organs in contact with the sling, characterized in that the sling is additionally provided with two lateral extensions (10) of the band (2) used to fix with a suture the sling to the urethra/bladder neck.

21. A kit for treatment of urinary incontinence comprising at least one sling according to claim 1, packaged in a sterile manner.

22. A sling for treatment of urinary incontinence comprising a band comprising a middle part and two opposing end parts characterized in that said sling includes, on said middle part, at least one pad of a biocompatible polymer affixed to said band and having a thickness at least twice as great as the thickness of said band, and said end parts are equipped with securing means, whereby said sling is implantable within a patient and said pad is capable of reducing or eliminating friction between said sling and organs in contact therewith, wherein said pad further comprises a covering of microporous biocompatible material.

23. The sling according to claim 22, characterized in that said pad comprises silicone foam.

24. A sling for treatment of urinary incontinence comprising a band comprising a middle part and two opposing end parts characterized in that said sling includes, on said middle part, at least one pad of a biocompatible polymer affixed to said band and having a thickness at least twice as great as the thickness of said band, and said end parts are equipped with securing means, whereby said sling is implantable within a patient and said pad is capable of reducing or eliminating friction between said sling and organs in contact therewith, wherein said band comprises silicone with a polyester mesh reinforcement.

25. The sling according to claim 24, further comprising at least one visual marker.

26. The sling according to claim 24, further comprising a radiopaque marker.

27. The sling according to claim 24, wherein said band further comprises a pair of opposed lateral extensions at about the midpoint of said middle part whereby said band is capable of being secured to a patient's urethra or bladder neck.

28. The sling according to claim 24, further comprising autofixable means.

* * * * *